United States Patent
Tang et al.

(10) Patent No.: US 11,320,428 B2
(45) Date of Patent: May 3, 2022

(54) PROBE FOR DUAL-MODE BIO-IMAGING

(71) Applicant: THE HONG KONG UNIVERSITY OF SCIENCE AND TECHNOLOGY, Hong Kong (CN)

(72) Inventors: Benzhong Tang, Hong Kong (CN); Meijuan Jiang, Hong Kong (CN); Xuesong Li, Hong Kong (CN); Jianan Qu, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 399 days.

(21) Appl. No.: 16/604,894

(22) PCT Filed: Apr. 18, 2018

(86) PCT No.: PCT/CN2018/083531
§ 371 (c)(1),
(2) Date: Oct. 11, 2019

(87) PCT Pub. No.: WO2018/192521
PCT Pub. Date: Oct. 25, 2018

(65) Prior Publication Data
US 2021/0190776 A1    Jun. 24, 2021

Related U.S. Application Data

(60) Provisional application No. 62/602,314, filed on Apr. 20, 2017.

(51) Int. Cl.
*G01N 33/543*    (2006.01)
*C07D 213/57*    (2006.01)
(Continued)

(52) U.S. Cl.
CPC ..... *G01N 33/54366* (2013.01); *A61B 5/0071* (2013.01); *A61B 5/0075* (2013.01);
(Continued)

(58) Field of Classification Search
CPC ................. C07D 213/57; C09K 11/06; C09K 2211/1018; G01N 33/54366;
(Continued)

(56) References Cited

U.S. PATENT DOCUMENTS

2014/0348753 A1    11/2014    Tang et al.

FOREIGN PATENT DOCUMENTS

| WO | 2013029340 A9 | 3/2013 |
|---|---|---|
| WO | 2016165616 A1 | 10/2016 |
| WO | 2017008743 A1 | 1/2017 |

OTHER PUBLICATIONS

Li, Xuesong et al., "Mitochondrial Imaging with Combined Fluorescence and Stimulated Raman Scattering Microscopy Using a Probe of the Aggregation-Induced Emission Characteristic", J. Am. Chem. Soc., vol. 139, Nov. 7, 2017.

*Primary Examiner* — Jennifer Wecker
*Assistant Examiner* — Kathryn Elizabeth Limbaugh
(74) *Attorney, Agent, or Firm* — Nath, Goldberg & Meyer; Joshua B. Goldberg

(57) ABSTRACT

The present subject matter relates to compounds that have aggregation-induced emission (AIE) characteristics and are capable of generating Raman signals in the Raman cell-silent region (1800 $cm^{-1}$-2800 $cm^{-1}$). The compounds can be used in dual-mode cell imaging by fluorescence and Raman microscopes.

15 Claims, 7 Drawing Sheets
(7 of 7 Drawing Sheet(s) Filed in Color)

(51) Int. Cl.
*C09K 11/06* (2006.01)
*G01N 21/64* (2006.01)
*A61B 5/00* (2006.01)
*G01N 33/533* (2006.01)

(52) U.S. Cl.
CPC ............ *C07D 213/57* (2013.01); *C09K 11/06* (2013.01); *G01N 21/6428* (2013.01); *G01N 21/6458* (2013.01); *G01N 33/533* (2013.01); *C09K 2211/1018* (2013.01)

(58) Field of Classification Search
CPC ............. G01N 33/533; G01N 21/6428; G01N 21/6458; A61B 5/0071; A61B 5/0075
See application file for complete search history.

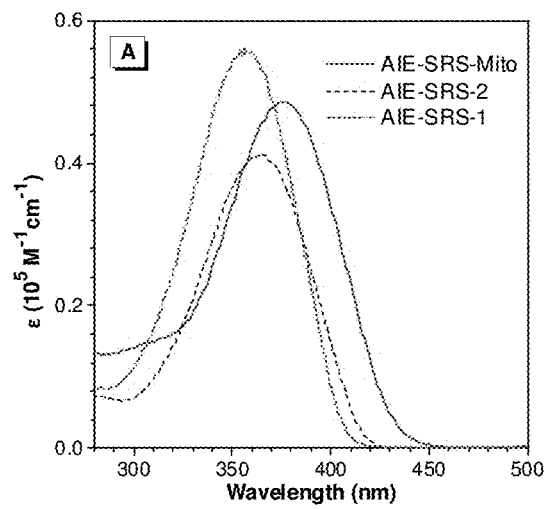
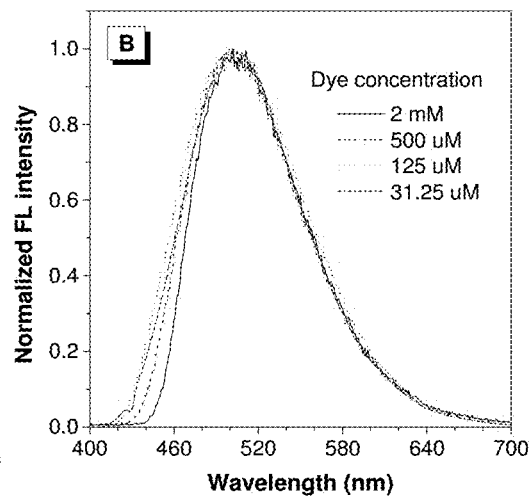
Fig. 1A
Fig. 1B
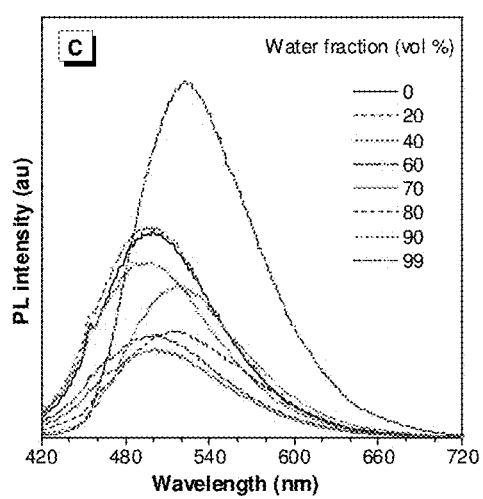
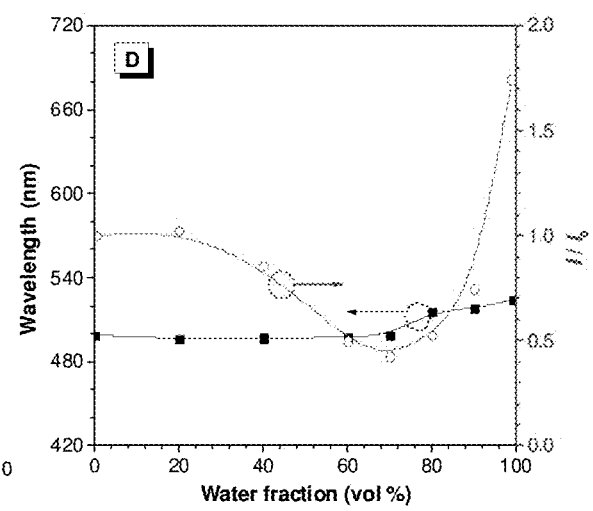
Fig. 1C
Fig. 1D

PROBE FOR DUAL-MODE BIO-IMAGING

This is a National Phase Application filed under 35 U.S.C. 371 as a national stage of PCT/CN2018/083531, filed Apr. 18, 2018, an application claiming the benefit from the U.S. Provisional Patent Application No. 62/602,314, Apr. 20, 2017, the content of each of which is hereby incorporated by reference in its entirety.

FIELD

The present subject matter relates generally to a series of compounds with aggregation-induced emission characteristics and Raman signals in the Raman cell-silent region (i.e., 1800 $cm^{-1}$-2800 $cm^{-1}$) and their applications in dual-mode bioimaging using fluorescence and Raman microscopy.

BACKGROUND

To elucidate the biological function of fluorescent probes or drugs, it is important to obtain a detailed picture of their intracellular distribution (local concentration) and their evolution with time. Fluorescence methods are suitable for this purpose because of their high sensitivity, specificity and spatiotemporal resolution. Fluorescence probes, such as Rhodamine 123 and JC-1, are often used for labeling one or more cellular targets of interest, e.g., molecules of interest or cellular organelles. However, due to the heterogeneity of cells, the dye concentration accumulated in organelles, especially mitochondria, can be extremely high. For example, based on the electrophoresis effect driven by the large mitochondria membrane potential (~180 mV), the concentration of cationic lipophilic molecules in the mitochondrion matrix was estimated to be up to 1000 folds higher than that in the cytoplasm. Such high concentrations lead to fluorescence quenching, in the case of Rhodamine 123, or formation of J-aggregates with a redder emission color, in the case of JC-1, which lead to reduced imaging contrast and a distortion of the linear relationship of the fluorescence intensity and dye concentration. Under these circumstances, unreliable results are often obtained.

Fluorescent probes with aggregation-induced emission (AIE) characteristics can circumvent the fluorescence quenching effect achieved when traditional fluorescent dyes, such as fluorescein and Rhodamine 123, are in an aggregated state. Unlike traditional fluorescent dyes, AIE fluorescent probes are typically weakly emissive in solution and exhibit a "turn-on" feature when aggregated or bound to targets. AIE fluorescent probes can show an ultrahigh imaging contrast, good photostability, and biocompatibility.

Recently, Raman microscopy has emerged as a powerful, non-invasive method to assess and image cellular chemical components. Raman microscopy is typically used to complement the fluorescence method and has become increasingly popular in biochemical and biomedicinal research. Raman microscopy possesses a label-free capability and provides rich chemical information from molecular vibrations. Competing spontaneous Raman imaging, coherent anti-stokes Raman scattering (CARS), and stimulated Raman scattering (SRS) imaging have emerged as newly developed techniques for fast Raman imaging in live cells. Specifically, SRS offers (i) greatly elevated Raman signal with a ~1,000 times faster speed than that of spontaneous Raman microscopy, (ii) excellent stability and reproducibility, (iii) no non-resonant background, (iv) linear concentration dependence and (v) high spectral resemblance with spontaneous Raman spectra.

It has been determined, however, that images from label-free Raman imaging processes often exhibit low contrast. Thus, small biorthogonal imaging tags such as C-D (carbon-deuterium), triple bond (alkyne C≡C, cyano C≡N) with Raman signals in the cell-silent regions (i.e., 1800-2800 $cm^{-1}$), have been used for specific tracking of small biomolecules, such as DNA, lipids, amino acids, sugars, and drugs. Small volumes of these tags are considered to minimally perturb the behavior of the target small molecule compared to traditional fluorescent tags. More recently, stimulated Raman scattering (SRS) imaging of alkyne-tagged molecules was reported with a detection limit down to the level of 31 µM, making it promising for visualizing the intracellular distribution of the target molecules in live cells with non-invasiveness and high spatiotemporal resolution.

Traditionally, fluorescence was not compatible with Raman microscopy, since fluorescence would greatly elevate the background of the Raman signal. Recently, however, fluorescence microscopy has been successfully coupled with SRS microscopy.

Accordingly, dual-mode probes that can co-localize the two types of signals (Raman and fluorescence) in a live cell are highly desirable.

SUMMARY

The present subject matter relates to compounds that have aggregation-induced emission (AIE) characteristics and are capable of generating Raman signals in the Raman cell-silent region (i.e., 1800 $cm^{-1}$-2800 $cm^{-1}$). Accordingly, the compounds can be used in dual-mode cell imaging by both fluorescence and Raman microscopes. For example, the compounds can be useful as tags for labeling targets of interest for biomedical studies. In particular, the compounds can be useful as mitochondrion targeting probes.

In an embodiment, the compounds have a backbone structural formula selected from the group consisting of:

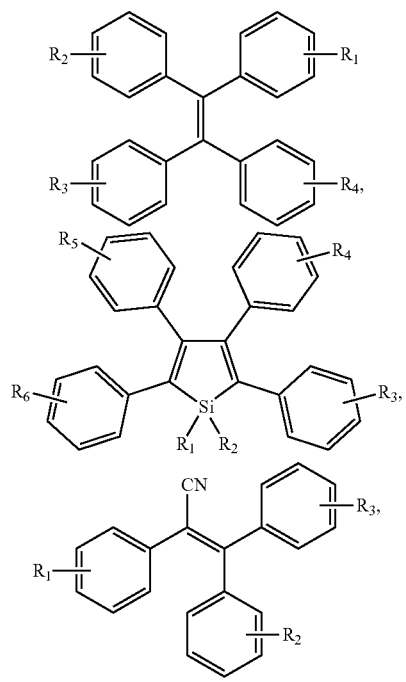

-continued

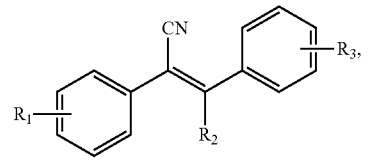

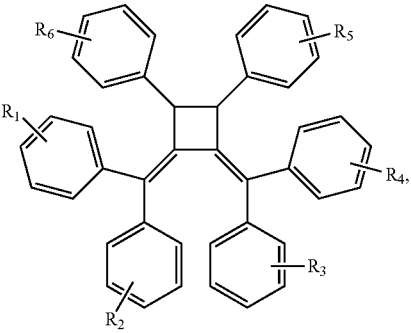

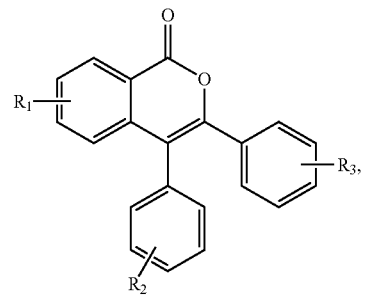

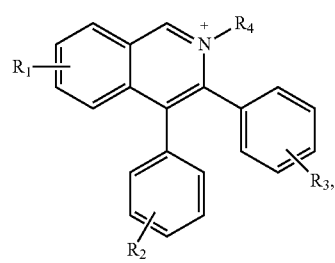

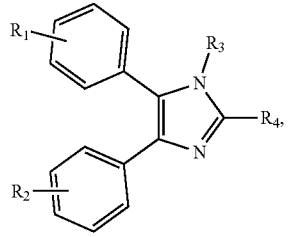

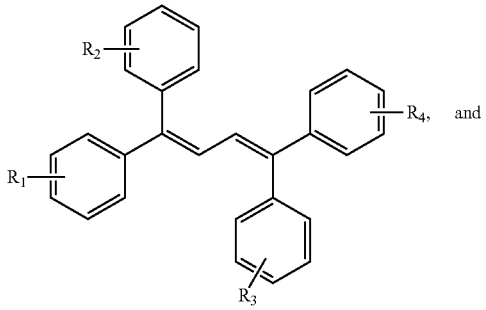 and

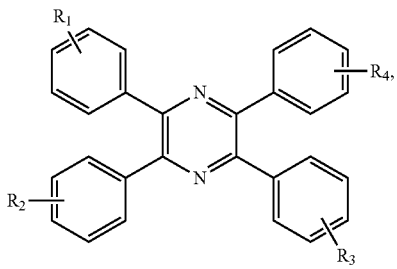

wherein each of $R_1$, $R_2$, $R_3$, $R_4$, $R_5$ and $R_6$ is independently selected from the group consisting of H,

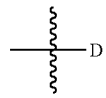

(deuterium),

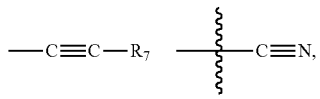

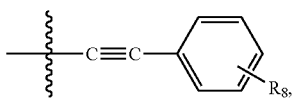

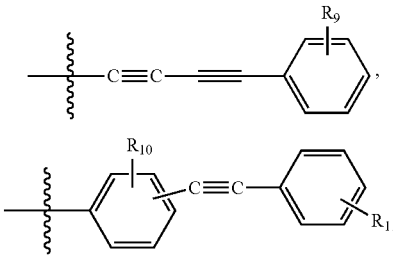

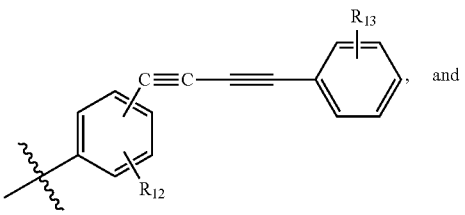, and

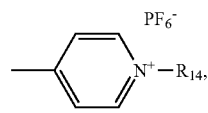

wherein at least one of $R_1$, $R_2$, $R_3$, $R_4$, $R_5$ and $R_6$ is other than H, and wherein $R_7$, $R_8$, $R_9$, $R_{10}$, $R_{11}$, $R_{12}$, $R_{13}$, and $R_{14}$ are independently selected from the group consisting of H, heteroatom, alkyl, unsaturated alkyl, heteroalkyl, cycloalkyl, heterocycloalkyl, aryl, and heteroaryl.

In a further embodiment, the compounds have the following backbone structural formula:

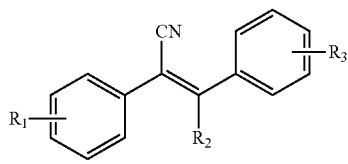

wherein each of $R_1$, $R_2$, $R_3$, $R_4$, $R_5$ and $R_6$ is independently selected from the group consisting of H,

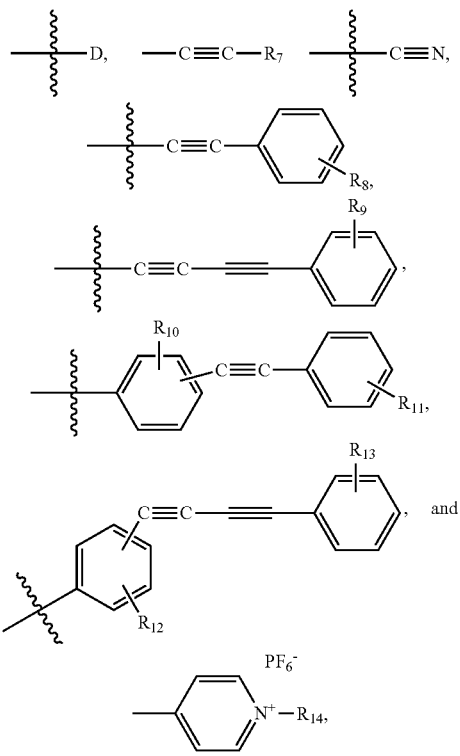

wherein at least one of $R_1$, $R_2$, $R_3$, $R_4$, $R_5$ and $R_6$ is other than H, and wherein $R_7$, $R_8$, $R_9$, $R_{10}$, $R_{11}$ and $R_{12}$, $R_{13}$, and $R_{14}$ are independently selected from the group consisting of H, heteroatom, alkyl, unsaturated alkyl, heteroalkyl, cycloalkyl, heterocycloalkyl, aryl, and heteroaryl.

In an embodiment, the compound is selected from:

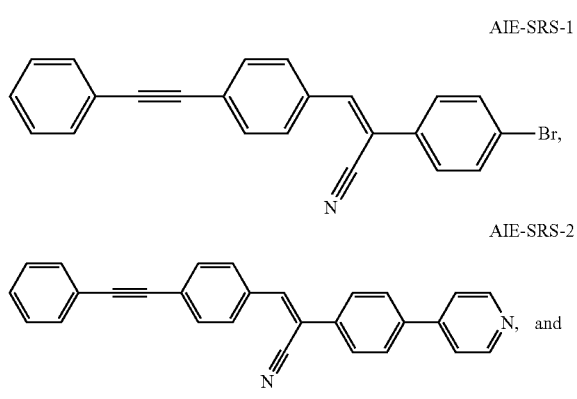

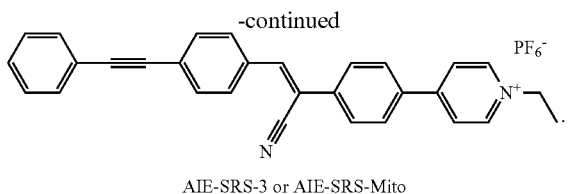

AIE-SRS-3 or AIE-SRS-Mito

BRIEF DESCRIPTION OF DRAWINGS

The file of this patent contains at least one drawing executed in color. Copies of this patent with color drawing(s) will be provided by the Patent and Trademark Office upon request and payment of the necessary fee.

Various embodiments will now be described in detail with reference to the accompanying drawings.

FIG. 1A depicts the UV-vis absorption spectra of AIE-SRS-Mito and its precursors (AIE-SRS-1 and AIE-SRS-2) in DMSO.

FIG. 1B depicts Fluorescence (FL) spectra of AIE-SRS-Mito in DMSO with different concentrations. Excitation wavelength=380 nm.

FIG. 1C depicts PL spectra of AIE-SRS-Mito in DMSO-water mixtures with various water fractions.

FIG. 1D depicts a plot of peak wavelength and peak intensity of AIE-SRS-Mito in DMSO-water mixtures versus water fraction (dye concentration=10 μM; excitation wavelength=400 nm).

DETAILED DESCRIPTION

Definitions

Figures 2A, 2B, 2C:
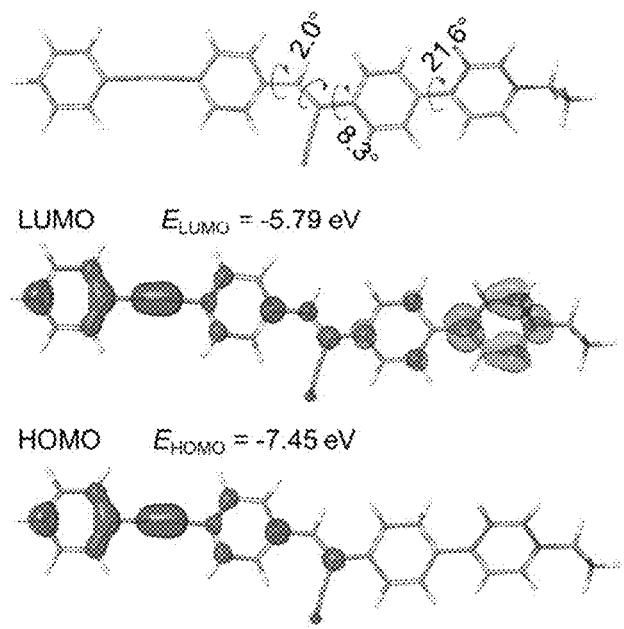
FIG. 2A depicts the optimized structure of AIE-SRS-Mito by DFT calculations at the base level of B3LYP/6-31G**.
FIG. 2B depicts the frontier orbital HOMO of AIE-SRS-Mito by DFT calculations at the base level of B3LYP/6-31G*.
FIG. 2C depicts the frontier orbital LUMO of AIE-SRS-Mito by DFT calculations at the base level of B3LYP/6-31G*.
Figures 3A, 3B, 3C, 3D, 3E, 3F:
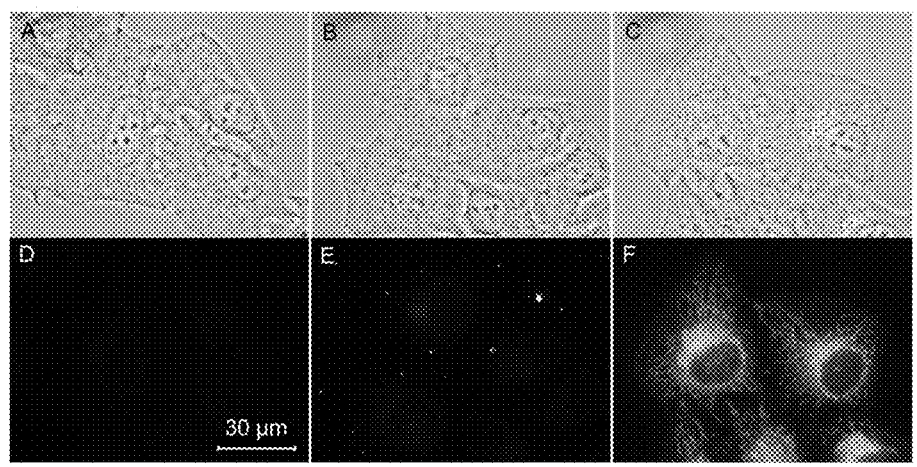
FIG. 3A depicts a bright field image of HeLa cells stained with 5 μM AIE-SRS-1 in culture medium for 20 minutes (excitation wavelength 330 nm-385 nm).
FIG. 3B depicts a bright field image of HeLa cells stained with 5 μM AIE SRS-2 in culture medium for 20 minutes (excitation wavelength 330 nm-385 nm).
FIG. 3C depicts a bright field image of HeLa cells stained with 5 μM AIE SRS-Mito in culture medium for 20 minutes (excitation wavelength 330 nm-385 nm).
FIG. 3D depicts a fluorescent image of HeLa cells stained with 5 μM AIE-SRS-1 in culture medium for 20 minutes (excitation wavelength 330 nm-385 nm).
FIG. 3E depicts a fluorescent image of HeLa cells stained with 5 μM AIE SRS-2 in culture medium for 20 minutes (excitation wavelength 330 nm-385 nm).
FIG. 3F depicts a fluorescent image of HeLa cells stained with 5 μM AIE SRS-Mito in culture medium for 20 minutes (excitation wavelength 330 nm-385 nm).

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

The term "$\lambda_{ex}$" as used herein refers to excitation wavelength.

The phrase "aggregation caused quenching" or "ACQ" as used herein refers to the phenomenon wherein the aggregation of π-conjugated fluorophores significantly decreases the fluorescence intensity of the fluorophores. The aggregate formation is said to "quench" light emission of the fluorophores.

The phrase "aggregation induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

"Emission intensity" as used herein refers to the magnitude of fluorescence/phosphorescence normally obtained from a fluorescence spectrometer or fluorescence microscopy measurement; "fluorophore" or "fluorogen" as used herein refers to a molecule which exhibits fluorescence; "luminogen" or "luminophore" as used herein refers to a molecule which exhibits luminescence; and "AIEgen" as used herein refers to a molecule exhibiting AIE characteristics.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein.

An alkenyl group is generally not substituted with another alkenyl group, an alkyl group, or an alkynyl group.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., $-C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine Noxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH2, SiH(alkyl), Si(alkyl)2, SiH(arylalkyl), Si(arylalkyl)2, or Si(alkyl)(aryl-alkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Probes for Dual-Mode Bio-Imaging

The present subject matter contemplates probes for dual-mode bio-imaging. Such probes can include compounds useful as both Raman and fluorescence imaging probes. The compounds exhibit aggregation induced emission (AIE) properties and produce Raman signals in the cell-silent regions (i.e., 1800 $cm^{-1}$-2800 $cm^{-1}$). The compounds can be used for mitochondria-targeting imaging with high contrast, under either or both of a fluorescence and stimulated Raman microscope. The compounds can successfully achieve ultra-high imaging contrast, good photo stability, and biocompatibility in bioimaging.
According to an embodiment, the compounds have a backbone structural formula selected from the group consisting of:
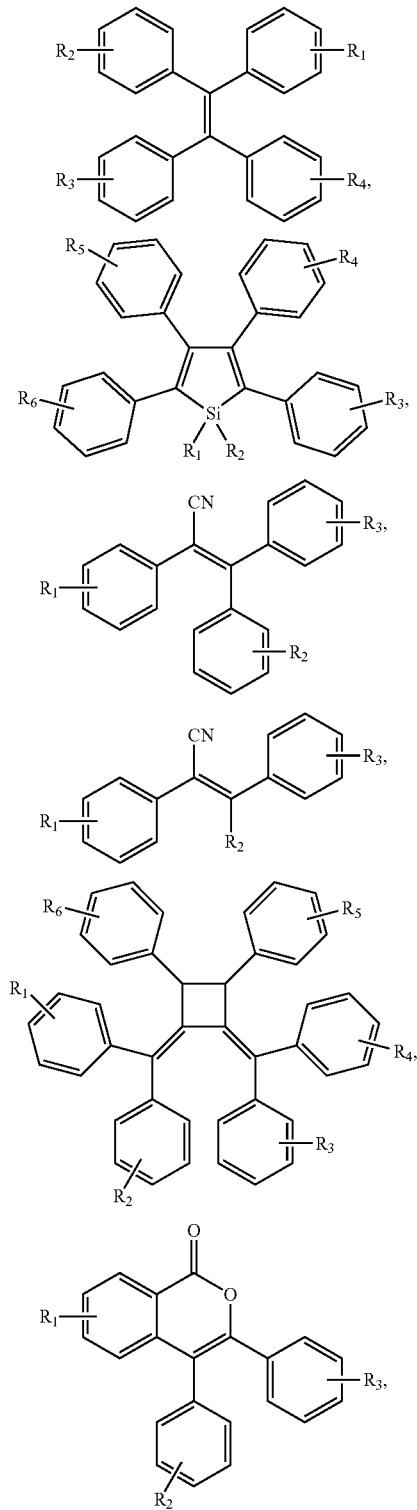
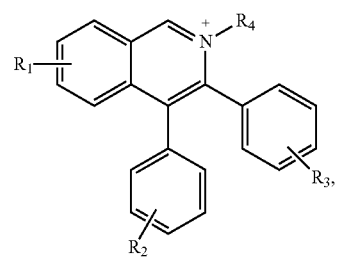
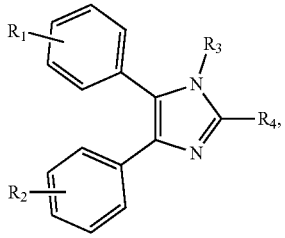
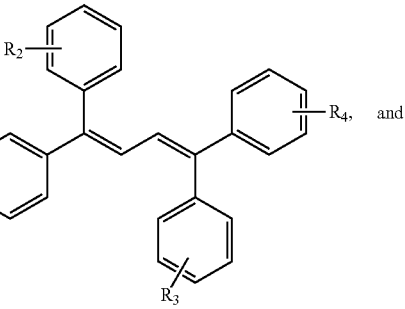
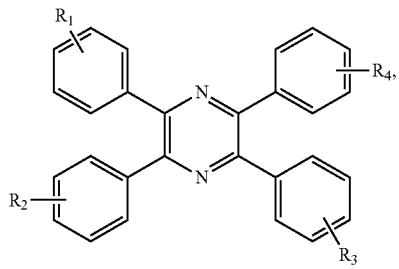
wherein each of $R_1$, $R_2$, $R_3$, $R_4$, $R_5$ and $R_6$ is independently selected from the group consisting of H,
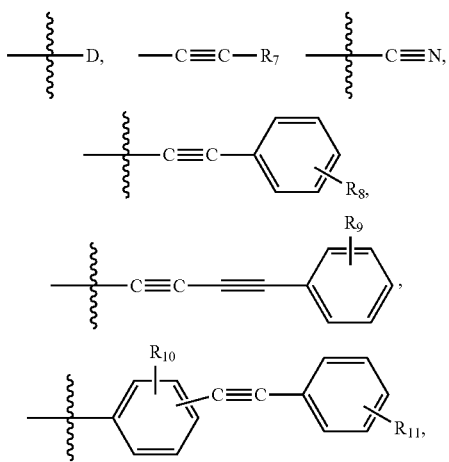

-continued

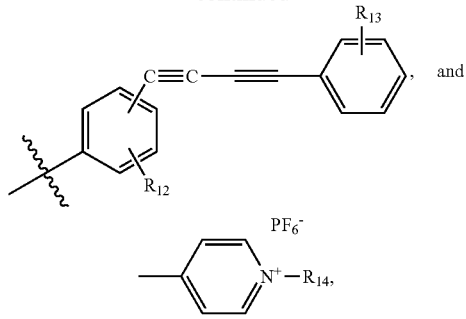

wherein at least one of $R_1$, $R_2$, $R_3$, $R_4$, $R_5$ and $R_6$ is other than H, and wherein $R_7$, $R_8$, $R_9$, $R_{10}$, $R_{11}$, $R_{12}$, $R_{13}$, and $R_{14}$ are independently selected from the group consisting of H, heteroatom, alkyl, unsaturated alkyl, heteroalkyl, cycloalkyl, heterocycloalkyl, aryl, and heteroaryl.

According to an embodiment, the compounds comprise the following structural formula:

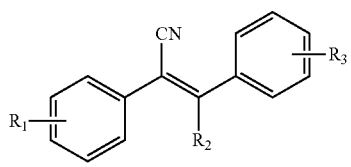

wherein each of $R_1$, $R_2$, $R_3$, $R_4$, $R_5$ and $R_6$ is independently selected from the group consisting of H,

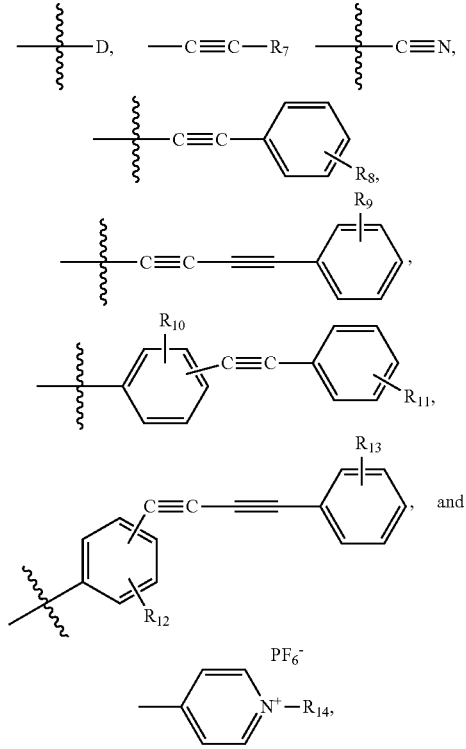

wherein at least one of $R_1$, $R_2$, $R_3$, $R_4$, $R_5$ and $R_6$ is other than H, and wherein $R_7$, $R_8$, $R_9$, $R_{10}$, $R_{11}$ and $R_{12}$, $R_{13}$, and $R_{14}$ are independently selected from the group consisting of H, heteroatom, alkyl, unsaturated alkyl, heteroalkyl, cycloalkyl, heterocycloalkyl, aryl, and heteroaryl.

In an embodiment, the compounds are selected from:

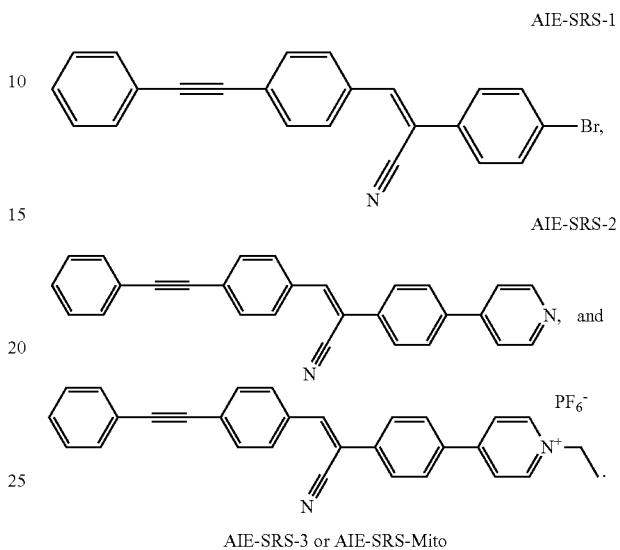

An exemplary reaction scheme is as provided below:

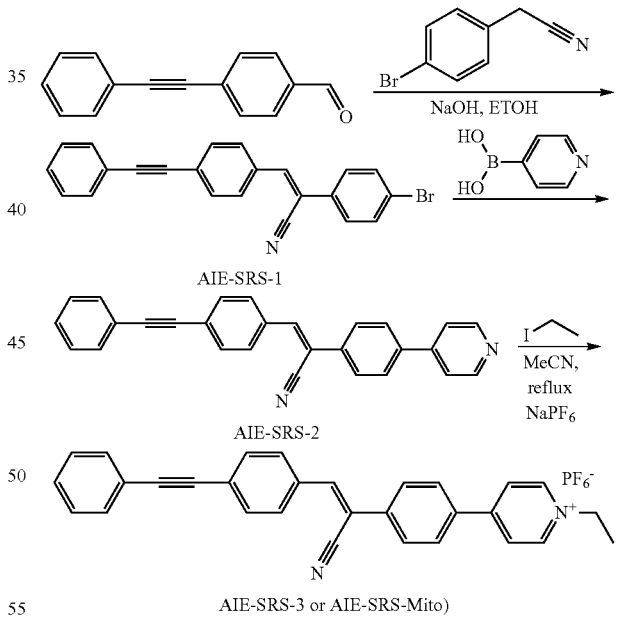

The method shown here is similar to the synthesis method using ASCP, above, except that the 4-(dimethylamino)benzaldehyde is replaced with commercially available 4-(phenylethynyl)benzaldehyde. As shown in the alternative reaction scheme, the method for preparing the present compounds can include the following sequential steps: Knoevenagel condensation, Suzuki coupling, and alkylation. The structures of AIE-SRS-Mito and its synthetic precursors (AIE-SRS-1 and AIE-SRS-2) were confirmed by 1H NMR, 13C NMR and high-resolution mass spectra with satisfactory results.

Identifying Targets of Interest

According to an embodiment, one or more of the present compounds can be contacted with a target cell to identify a target of interest in the target cell, e.g., to detect a presence or absence of a target of interest. The target of interest can be identified by an imaging method, such as fluorescence microscopy and/or Raman microscopy. The target of interest can include at least one of a biomolecule, a drug, a protein, and a cellular organelle of the target cell. According to an embodiment, the target of interest is a cellular organelle. According to an embodiment, the target of interest is a mitochondrion in the target cell.

According to an embodiment the imaging method can include both fluorescence microscopy and Raman microscopy, or either on its own. According to an embodiment, the Raman microcopy can include at least one of spontaneous Raman scattering microscopy, stimulated Raman scattering microscopy, and coherent anti-stokes Raman scattering microscopy. According to an embodiment, the fluorescence microscopy can include at least one of fluorescence microscopy, confocal microscopy, and two-photon excitation microscopy. According to an embodiment, an intracellular concentration of the compound can be determined qualitatively from a fluorescence intensity. According to an embodiment, an intracellular concentration of the compound can be determined quantitatively from a stimulated Raman scattering signal intensity.

According to an embodiment, the present compounds can be used as probes for dual-mode bio-imaging. According to an embodiment, the present compounds can be used for mitochondria-targeting imaging with high contrast, both under a fluorescence and stimulated Raman microscope. The present compounds possess AIE features and are capable of generating biorthogonal Raman signals. The present compounds can successfully achieve ultrahigh imaging contrast, good photostability, and biocompatibility in bioimaging. For example, target cells can be incubated with a concentration of up to 40 µM of the present compounds for up to 40 minutes to provide mitochondrial selective staining, with low cytotoxicity and good biocompatibility.

The present teachings are illustrated by the following examples.

EXAMPLES

Materials and Instruments

Minimum essential medium (MEM), fetal bovine serum (FBS), penicillin and streptomycin and Mitotracker Red FM were purchased from Invitrogen. 3-(4, 5-Dimethylthiazol-2-yl)-2, 5-diphenyltetrazolium bromide (MTT), other chemicals and solvents were all purchased from Sigma-Aldrich and used as received without further purification. Milli-Q water was supplied by Milli-Q Plus System (Millipore Corporation, Breford, USA). Milli-Q water (18.2 MΩ) was used to prepare the buffer solutions. 1×PBS contains NaCl (137 mM), KCl (2.7 mM), Na2HPO4 (10 mM), and $KH_2PO_4$ (1.8 mM). 1H and $^{13}$C NMR spectra were measured on a Bruker ARX 400 NMR spectrometer using d6-DMSO and $CDCl_3$ as solvents and tetramethylsilane (TMS) as internal reference. High-resolution mass spectra (HR-MS) were recorded on a Finnigan MAT TSQ 7000 Mass Spectrometer System operating in a MALDI-TOF mode. UV absorption spectra were taken on a Milton Ray Spectronic 3000 array spectrophotometer. Photoluminescence (PL) spectra were recorded on a Perkin-Elmer spectrofluorometer LS 55. Theoretical Calculations were performed at the B3LYP/6-31G** level of theory for geometry optimizations, HOMO and LUMO in Schrödinger program.

For cell culturing, HeLa cells were cultured in the MEM containing 10% FBS and antibiotics (100 units/mL penicillin and 100 g/mL streptomycin) in a humidity incubator with an atmosphere of 5% $CO_2$ at 37° C. and subcultured every 2-3 days.

For cell imaging, HeLa cells were grown overnight on a 35-mm petri dish with a cover slip. The cover slip was mounted to an iron slide with observation window. The staining solution was prepared by adding the dye stock solution (10 mM in DMSO) in to 2 mL of cell medium. Before imaging, the cells were stained with 2 mL of dye solution for a certain time and then imaged under an FL microscope (BX41 upright Microscope) using different combinations of excitation and emission filters for each dye.

For cell viability evaluated by MTT assay, cells were seeded in 96-well plates at a density of 10000 cells per well. After 24 h incubation, medium in each well was replaced by 100 µL fresh medium containing different concentrations of AIE-SRS-Mito. After 24 hours of treatment, into each well, 10 µL MTT solution (5 mg/mL in PBS) was added. After 4 hours of incubation, the MTT-containing solution was gently removed and replaced with 100 µL of DMSO. After agitation, the absorption of each well at 490 nm was recorded via a plate reader (Perkin-Elmer Victor3™). Each of the experiments were performed for 6 wells parallel. The background of the blank was subtracted and the cell viability of the control group was set to unity.

Example 1

Synthesis of AIE-SRS-1

Into a 100 mL round bottom flask were dissolved 4-(phenylethynyl)benzaldehyde (206 mg, 1 mmol) and 4-bromophenylacetonitrile (196 mg, 1 mmol) in 40 mL ethanol to form a mixture. Sodium hydroxide (100 mg) was added to the mixture. After stirring for 5 h at 50° C., the resulting pale yellow precipitates were filtered and washed with cold ethanol. The product was dried and weighted. Yield: 95%. $^1$H-NMR (400 MHz, $d_6$-DMSO) δ (ppm) 8.13 (s, 1H), 8.00 (d, 2H, J=8.0 Hz), 7.74-7.71 (m, 6H), 7.60-7.58 (m, 2H), 7.46-7.45 (m, 3H). $^{13}$C NMR (100 MHz, $d_6$-DMSO) δ (ppm) 142.4, 133.6, 133.0, 132.1, 131.9, 131.5, 129.5, 129.2, 128.8, 127.9, 124.4, 122.8, 121.9, 117.5, 109.8, 91.8, 89.0. MS (MALDI-TOF): calculated for AIE-SRS-1 ($C_{23}H_{14}BrN$): 383.0310, found: 383.0309.

Example 2

Synthesis of AIE-SRS-2

Into a 100 mL two-necked round bottom flask equipped with a condenser were added 1 (192 mg, 0.5 mmol), 4-pyridinylboronic acid (74 mg, 0.6 mmol), potassium carbonate (172 mg, 1.25 mmol) and Pd(PPh3)4 (10 mg, 0.01 mmol) in 10 mL and 3 mL water under nitrogen to form a mixture. The mixture was stirred and heated to reflux overnight. After cooling to room temperature and evaporating THF, the mixture was extracted with dichloromethane (DCM) three times. The organic phase was collected, washed with water and dried over anhydrous magnesium sulfate. After solvent evaporation, the crude product was purified by silica-gel column chromatography using DCM/MeOH as eluent. Yield: 99%. $^1$H NMR (400 MHz, $CDCl_3$)

δ (ppm) 8.71 (d, 2H, J=4.4 Hz), 7.93 (d, 2H, J=8.4 Hz), 7.82 (d, 2H, J=8.4 Hz), 7.74 (d, 2H, J=8.4 Hz), 7.63 (d, 2H, J=8.4 Hz), 7.60-7.54 (m, 5H), 7.39-7.36 (m, 3H). $^{13}$C NMR (100 MHz; CDCl$_3$) δ (ppm) 150.7, 147.3, 141.9, 139.2, 135.3, 133.3, 132.3, 132.0, 129.6, 129.0, 128.7, 127.9, 127.0, 126.1, 123.0 121.7, 117.9, 111.4. MS (MALDI-TOF): calculated for AIE-SRS-2 (C$_{28}$H$_{18}$N$_2$): 382.1470, found: 382.1467.

Example 3

Synthesis of AIE-SRS-Mito (AIE-SRS-3)

Into a 100 mL two-necked round bottom flask were dissolved 2 (100 mg, 0.26 mmol) in 10 mL acetonitrile. Iodoethane (0.1 mL, 1.25 mmol) was then added and the mixture was heated to reflux overnight. After cooling to room temperature, 20 mL diethyl ether was added in portions. The yellow precipitates formed were filtered and washed with diethyl ether. The precipitates were redissolved in acetone and mixed with saturated NaPF$_6$ solution (5 mL). After stirring for 1 h, acetone was evaporated. The resulting light-yellow precipitate was filtered again, washed with water dried under reduced pressure. Yield: 70%. $^1$H NMR (400 MHz, d$_6$-DMSO) δ (ppm) 10.35 (s, 1H), 8.75 (d, 1H, J=8.8 Hz), 8.30-8.26 (m, 2H), 7.73 (d, 1H, J=8.0 Hz), 7.60-7.42 (m, 9H), 7.30-7.24 (m, 5H), 7.10 (d, 1H, J=8.0 Hz), 4.43 (t, 2H, J=7.2 Hz), 4.01 (s, 3H) 1.89-1.84 (m, 2H), 0.82 (t, 3H, J=7.2 Hz). $^{13}$C NMR (100 MHz, d$_6$-DMSO) δ (ppm) 153.3, 144.6, 143.6, 137.0, 134.0, 133.5, 131.9, 131.5, 129.7, 128.9, 126.9, 124.7, 124.5, 121.8, 117.5, 109.7, 92.1, 89.0, 55.6, 16.3. 31P-NMR (162 MHz, d$_6$-DMSO) δ (ppm) −131.0, 135.4, 139.8, 144.2, 148.6, 153.0, 157.4. 19F-NMR (376 MHz, d$_6$-DMSO) δ (ppm) −69.2, 71.0. MS (MALDI-TOF): calculated for cation of AIE-SRS-3 (C$_{30}$H$_{23}$N$_2^+$): 411.1856, found: 411.1860. MS (MALDI-TOF): calculated for cation of AIE-SRS-3 (PF$_6$—): 144.9647, found: 144.9639.

Example 4

Photophysical Properties

After confirmation of the structure by $^1$H NMR, $^{13}$C NMR, and high resolution mass spectra with satisfactory results, the photophysical properties of AIE-SRS-Mito were investigated. As shown in FIG. 1A, AIE-SRS-Mito exhibits an absorption band at around 380 nm with a red-shift from its synthetic precursors. The red-shift can be attributed to the extension of π-conjugation and enhanced electron-accepting property of pyridinium salts. On the other hand, the fluorescence emission band of AIE-SRS-Mito was located at around 500 nm with a large Stokes shift of 120 nm (FIG. 1B), indicating an occurrence of twisted intramolecular charge transfer (TICT) of such donor-π-acceptor molecule. Because of such a large Stokes shift, only a slight inner-filter effect was observed with the increase of concentration from 31.25 μM to 2 mM as there was little change in the peak wavelength and a slight decrease in intensity below 480 nm.

Then AIE-SRS-Mito was studied in DMSO-water mixtures with different water fractions. As shown in FIGS. 1C-1D, the emission peak intensity was decreased with the increase of water fraction from 0 to 70 vol % due the quenching effect of the highly polar water. Due to poor solubility of AIE-SRS-Mito in water, a further increase in the water fraction lead to the aggregation/precipitation of dye molecules and an increase of fluorescence intensity. This is a typical AIE phenomenon, as the free intramolecular rotations of the excited molecules were restricted upon aggregation, thus blocking the non-radiative decays and favoring the radiative decay. Only a slight red-shift in peak wavelength was observed and this should be attributed to the increased solution polarity by increasing water fraction. The AIE feature and TICT effect upon excitation were further verified by the theoretical calculations (FIGS. 2A-2C). Results revealed the twisted conformation of AIE-SRS-Mito in its optimized structure like other AIEgens and also that there is a substantial shift of electron cloud from HOMO to LUMO, suggesting the great probability of occurrence of TICT.

Example 5

Mitochondrial-S Elective Staining

To verify the mitochondrial specificity of AIE-SRS-Mito, cellular imaging was first conducted by incubating HeLa cells with 5 μM AIE-SRS-Mito for 20 min. Compared to its synthetic precursors, AIE-SRS-Mito precursors exhibit good cell permeability with a strong blue fluorescence (FIGS. 3A-3F).

A co-localization experiment was then conducted using AIE-SRS-Mito and a commercial mitochondrial probe, Mitotacker Red (MTR) FM. The excitation wavelength was 330-385 nm for AIE-SRS-Mito and 540-580 nm for MTR. As shown in FIGS. 4A-4D, AIE-SRS-Mito stained the linear reticulum-like structures in cells with high contrast. The fluorescence of AIE-SRS-Mito was perfectly overlapped with the fluorescence of mitochondrial probe, Mitotacker Red FM, revealing good mitochondrial selectivity of AIE-SRS-Mito.

Figures 4A, 4B, 4C, 4D, 4E:
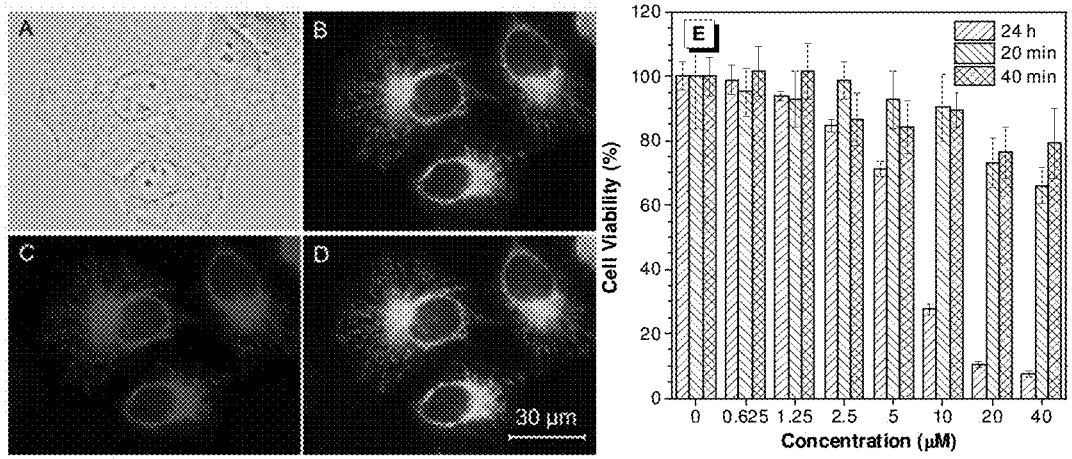
FIG. 4A depicts a bright field image of HeLa cells co-stained with AIE-SRS-Mito (5 μM) and Mitotracker Red FM (MTR, 100 nM) in culture medium for 20 min.
FIG. 4B depicts a fluorescent image of HeLa cells stained with AIE-SRS-Mito (5 μM) in culture medium for 20 min.
FIG. 4C depicts a fluorescent image of HeLa cells stained with Mitotracker Red FM (MTR, 100 nM) in culture medium for 20 min.
FIG. 4D depicts a merged image of FIGS. 4B and 4C.
FIG. 4E is a graph depicting cell cytotoxicity as evaluated by MTT assay.

Cell cytotoxicity was evaluated by MTT assay (FIG. 4E). HeLa cells were incubated with different concentrations of AIE-SRS-Mito for 24 hours. For example, HeLa cells were incubated with different concentrations of AIE-SRS-Mito for 20 or 40 min and then the medium was replaced with fresh medium, followed by further incubation for 24 hours. As shown in FIG. 4E, after incubation with AIE-SRS-Mito for 24 hours, cell viability was decreased with increased concentrations from 0 to 40 μM with a half maximal inhibitory concentration (IC$_{50}$) of ca. 7 μM. However, the results also show that cell viability remained over 70% upon treatment with <40 μM of AIE-SRS-Mito for <40 min, suggesting AIE-SRS-Mito can be used as a mitochondrial selective staining probe at such conditions with a low cytotoxicity and good biocompatibility.

Example 6

SRS and TPEF

Figures 5A, 5B, 5C, 5D:
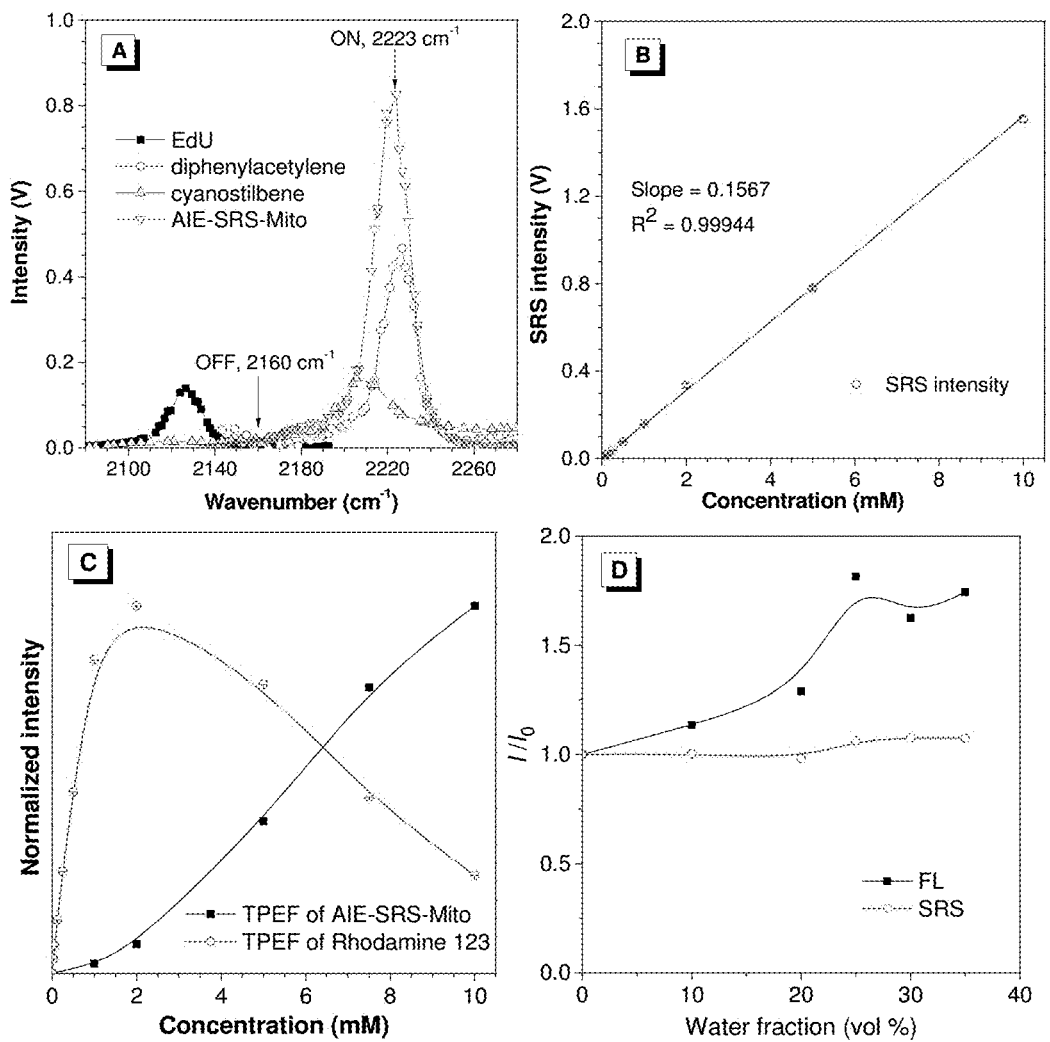
FIG. 5A shows the SRS spectra of EDU (5 mM in PBS) or AIE-SRS-Mito (5 mM in DMSO) in cell-silent region.
FIG. 5B shows change of SRS intensity $I_{SRS}$ of AIE-SRS-Mito with different concentrations (background from DMSO was subtracted, $I_{SRS}=I_{ON}-I_{OFF}$).
FIG. 5C shows change of two-photon excited fluorescence (TPEF) intensity of Rhodamine 123 and AIE-SRS-Mito with different concentrations (0-10 mM).
FIG. 5D shows TPEF and SRS of AIE-SRS-Mito (1 mM) in DMSO-water mixtures with different water fractions.

A FL-SRS microscope built by the inventors was used to carry out experiments on the Raman scattering signal of AIE-SRS-Mito after confirming the AIE characteristics and mitochondrial selectivity of AIE-SRS-Mito. Resembling its own Spontaneous Raman spectrum, AIE-SRS-Mito shows a Raman peak at 2223 cm$^{-1}$ in the-cell silent region, with a peak intensity of RIE=6.0 (FIG. 5A). Such a high RIE value can be attributed to the synergetic effect of the signals of diphenylacetylene (CC, 2225 cm$^{-1}$, RIE=3.2) and cyanostilbene (C≡N, 2206 cm$^{-1}$, RIE=1.3). The chemical structures of EdU, diphenyl acetylene and cyanostilbene are provided below.

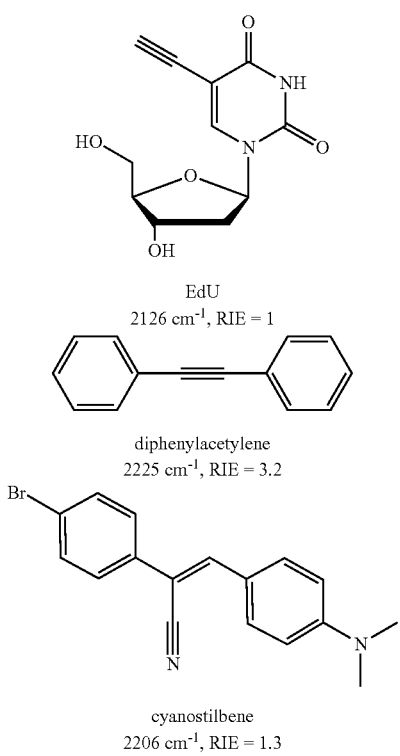

EdU
2126 cm$^{-1}$, RIE = 1 diphenylacetylene
2225 cm$^{-1}$, RIE = 3.2 cyanostilbene
2206 cm$^{-1}$, RIE = 1.3

To eliminate the influence of light reflection and scattering on the baseline, SRS intensity $I_{ON}$ at 2223 cm$^{-1}$ (resonance-on) and $I_{OFF}$ at 2160 cm$^{-1}$ (resonance-off) was used to calculate the SRS signal intensity $I_{SRS}=I_{ON}-I_{OFF}$. After subtracting the intrinsic $I_{SRS}=0.042$ V in pure DMSO (background), a linear relationship between SRS intensity $I_{SRS}$ and the dye concentration c was obtained as $I_{SRS}=0.1567c$ with $R^2=0.99944$ in the plot shown in FIG. 5B. The analytical detection limit and quantification limit were calculated to be 8.5 µM and 28.4 µM, respectively, indicating the high sensitivity of the SRS system. Further, the SRS spectra of AIE-SRS-Mito were collected at different concentrations in DMSO and no obvious shifts in the peak position was found, indicating the inertness of Raman signal to the concentration change. Due to the inert response of SRS signal to the change of environment, the linear plot of $I_{SRS}=0.1567c$ can act further as a calibration for the intracellular dye concentration by keeping the same signal collecting condition.

Figure 6:
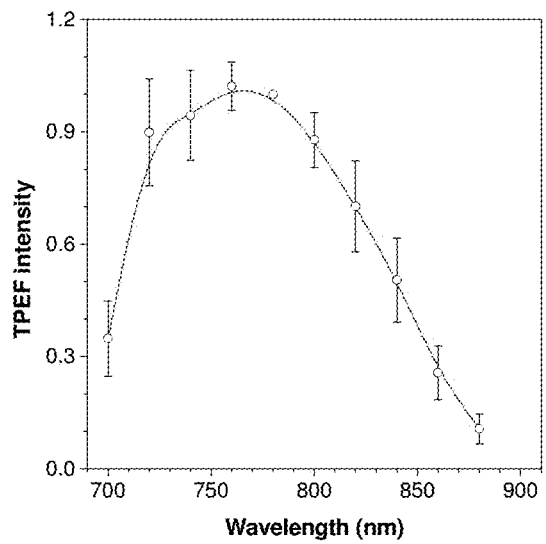
FIG. 6 is a plot of TPEF intensity versus excitation wavelength measured in live cells by using a two photon microscope with Ti:sapphire laser (laser power=5 mW).
Figures 7A, 7B, 7C, 7D:
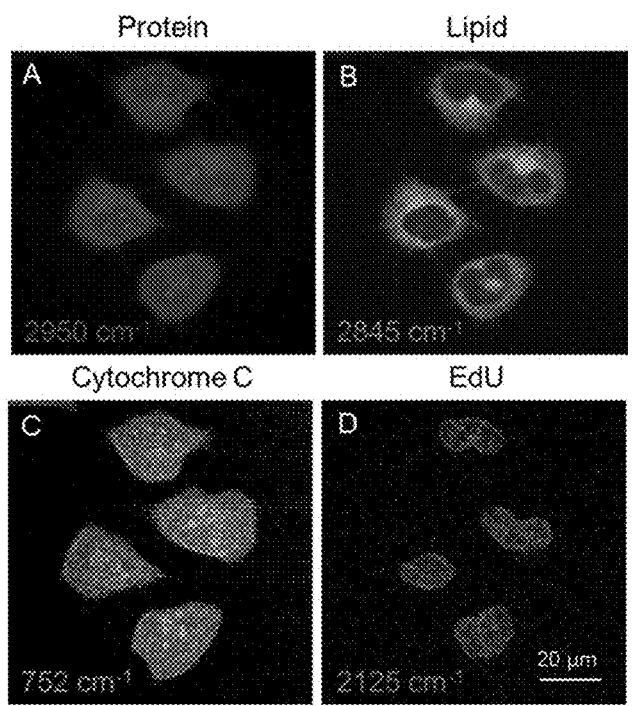
FIG. 7A depicts an SRS image of protein at 2950 cm$^{-1}$ in live HeLa cells.
FIG. 7B depicts an SRS image of lipid at 2845 cm$^{-1}$ in live HeLa cells.
FIG. 7C depicts an SRS image of cytochrome c at 752 cm$^{-1}$ in live HeLa cells.
FIG. 7D depicts an SRS image of DNA at 2125 cm-1 in live HeLa cells.

To deepen the understanding of the inertness of the SRS signal in comparison to the high sensitivity of fluorescence, two factors were examined: concentration and polarity. Two-photon excitation fluorescence (TPEF) was used for this demonstration due to the feasibility of the newly built FL-SRS system. A two photon microscope with Ti:sapphire laser (laser power=5 mW) was used and HeLa cells were stained with 5 µM of AIE-SRS-Mito for 30 min. The intensity of the image of 780 nm was set to unity. As a newly synthesized compound, the two-photon excitation peak wavelength was determined to be 780 nm for AIE-SRS-Mito (FIG. 6).

As shown in FIG. 5C, nonlinearities of FL intensity versus concentration were observed for both AIE-SRS-Mito and Rhodamine 123 in the range of 0-10 mM. The occurrence of fluorescence quenching of Rhodamine 123 was found to be lower than 1 mM, which may be caused by the self-absorption, collisions of excited molecules, formation of non-fluorescent excimers, etc. Meanwhile, AIE-SRS-Mito was found to be more resistant to fluorescence quenching in high concentrations. In terms of polarity effect, the TPEF and SRS signal were studied simultaneously in the DMSO-water mixtures at the concentration of 1 mM (FIG. 5D). With the increase of water fraction from 0 to 40 vol %, the SRS intensity shows little change while the TPEF intensity increased almost 70%. Further, increase of the water fraction lead to precipitation. The change of fluorescence intensity was opposite to previous results. This phenomenon can be attributed to the different concentrations used and excitation fashion. However, the detailed photophysical mechanisms remain unclear. Overall, the results demonstrated the high sensitivity of fluorescence intensity and inertness of SRS intensity to the change of concentration and surrounding environment, suggesting SRS is superior to fluorescence for concentration calibration in the heterogenous intracellular environment.

Example 7

SRS Imaging in Live Cells

SRS imaging was conducted with live HeLa cells to validate a newly built SRS imaging system. The DNA of HeLa cells were pre-labeled with EdU by incubation with 100 µM of EdU in culture medium for 22 hours to ensure sufficient cell-uptake. FIGS. 7A-7D show the distributions of protein, lipid, cytochrome c and DNA in HeLa cells at 2950 cm$^{-1}$, 2845 cm$^{-1}$, 752 cm$^{-1}$, and 2125 cm$^{-1}$, respectively.

Figures 8A, 8B, 8C, 8D:
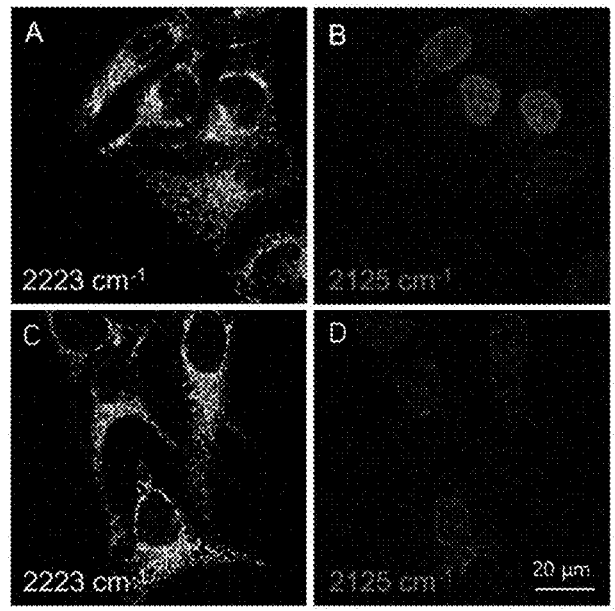
FIG. 8A depicts an SRS image of AIE-SRS-Mito in live HeLa cells.
FIG. 8B depicts an SRS image of EdU in live HeLa cells.
FIG. 8C depicts an SRS image of AIE-SRS-Mito in live HeLa cells.
FIG. 8D depicts an SRS image of EdU in live HeLa cells.
Figures 9A, 9B, 9C:
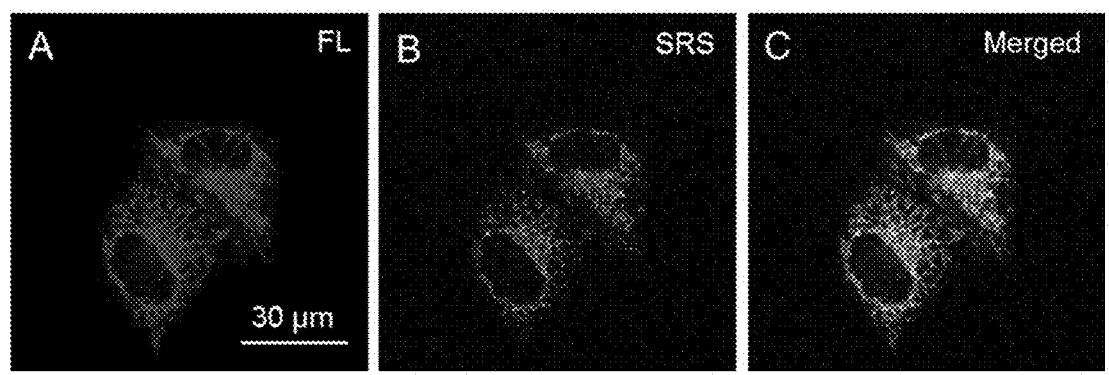
FIG. 9A depicts a TPEF image of HeLa cells stained with 20 μM AIE-SRS-Mito, the FL intensity is coded with a royal color bar.
FIG. 9B depicts an SRS image of HeLa cells stained with 20 μM AIE-SRS-Mito, the FL intensity is coded with a royal color bar.
FIG. 9C depicts a merged imaged of FIGS. 9A and 9B.

Due to the high Raman signal (RIE=6) and mitochondria targeting of AIE-SRS-Mito, AIE-SRS-Mito can serve as a mitochondrial probe for Raman microscopy. In previous reports, cytochrome c, an endogenous protein abundant in the mitochondria membrane, was used for visualization of the mitochondria. However, compared to the unclear and low-contrast image of mitochondria by cytochrome c (752 cm$^{-1}$, FIG. 7C), the SRS image of mitochondria in HeLa cells were obtained at 2223 cm$^{-1}$ with much more clear reticulum-like structures after incubated with 5 µM of AIE-SRS-Mito for 60 min (FIGS. 8A and 8C). Meanwhile, the nuclei of the Hela cells were prelabeled with EdU and imaged at 2125 cm$^{-1}$ (FIGS. 8B and 8D). The total discrepancy of the two signals demonstrated the compatibility of AIE-SRS-Mito with EdU for dual-color imaging. Compared to the uneven distribution of EdU among cells, AIE-SRS-Mito exhibits relatively even distribution with similar signal intensity. Due to good cell permeability, staining of AIE-SRS-Mito took a much shorter time than that of EdU for labeling. Overall, AIE-SRS-Mito serves as a superior mitochondrial probe for SRS imaging, with quick staining and good imaging contrast.

Example 8

FL-SRS Imaging

Figures 10A, 10B, 10C, 10D:
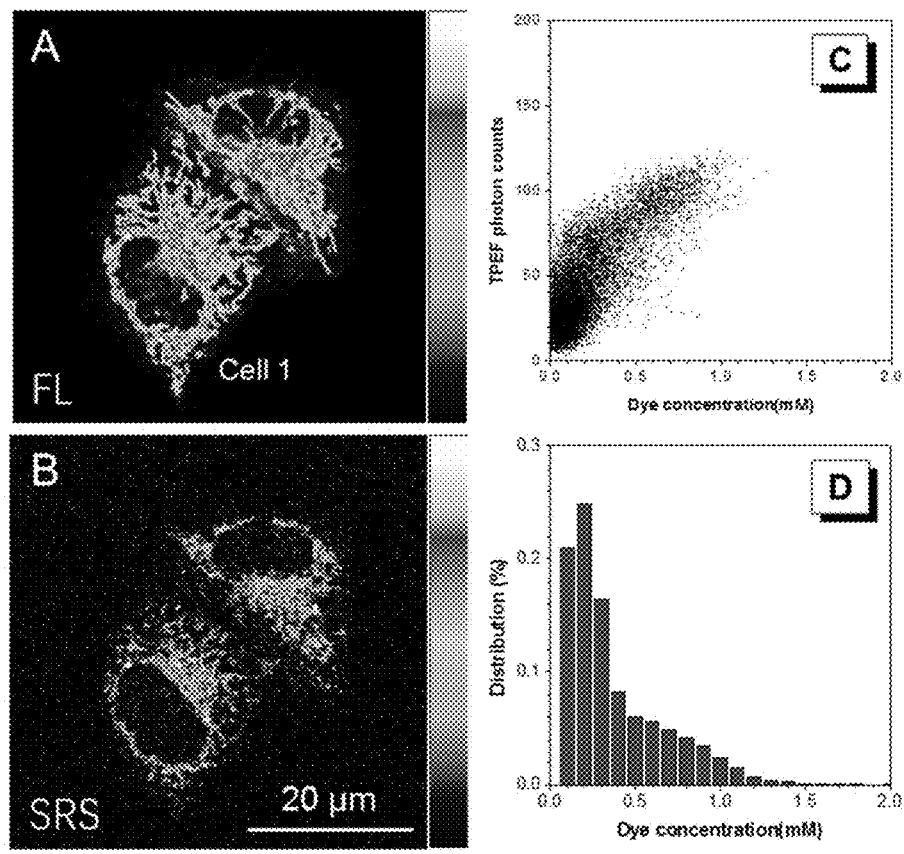
FIG. 10A depicts a TPEF image of HeLa cells stained with 20 μM AIE-SRS-Mito.
FIG. 10B is depicts an SRS image of HeLa cells stained with 20 μM AIE-SRS-Mito.
FIG. 10C is a graph showing the correlation of FL intensity and SRS intensity of Cell 1.
FIG. 10D is a histogram showing correlation of FL intensity and SRS intensity of Cell 1 (SRS intensity $I_{SRS}$ was interpreted as dye concentration c by the equation of $I_{SRS}=0.1567$ c).
Figures 11A, 11B, 11C, 11D, 11E, 11F:
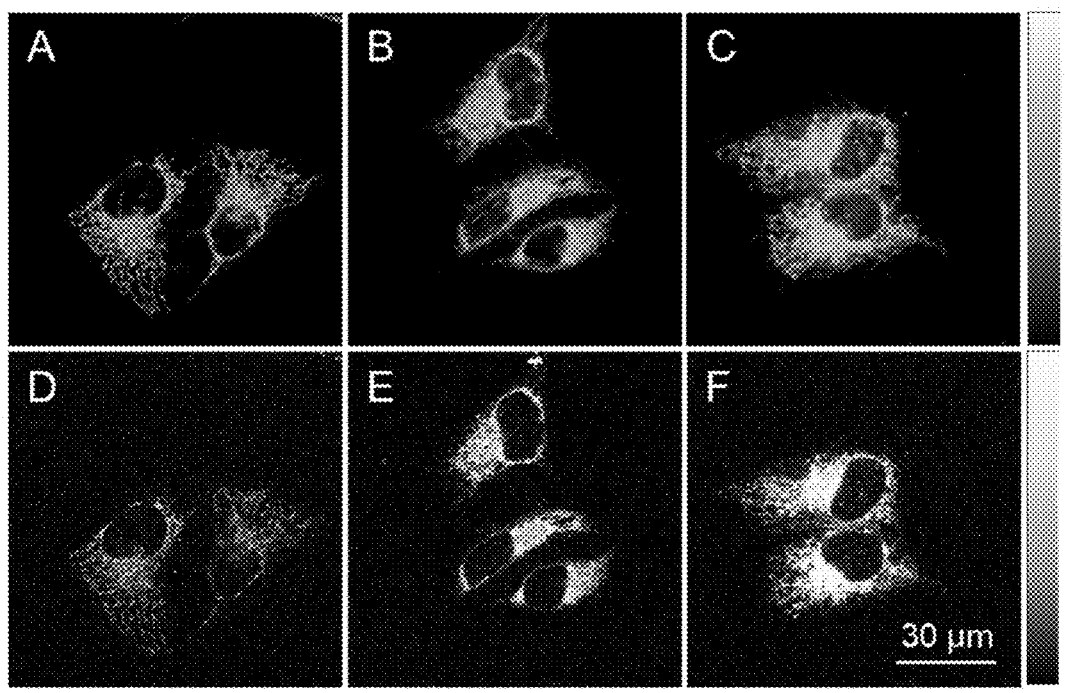
FIG. 11A is a fluorescent image of HeLa cells stained with 20 μM AIE-SRS-Mito for 30 minutes.
FIG. 11B is a fluorescent image of HeLa cells stained with 20 μM AIE-SRS-Mito for 60 minutes.
FIG. 11C is a fluorescent image of HeLa cells stained with 20 μM AIE-SRS-Mito for 105 minutes.
FIG. 11D is an SRS image of HeLa cells stained with 20 μM AIE-SRS-Mito for 30 minutes.
FIG. 11E is an SRS image of HeLa cells stained with 20 μM AIE-SRS-Mito for 60 minutes.
FIG. 11F is an SRS image of HeLa cells stained with 20 μM AIE-SRS-Mito for 105 minutes.
Figures 12A, 12B, 12C, 12D, 12E, 12F:
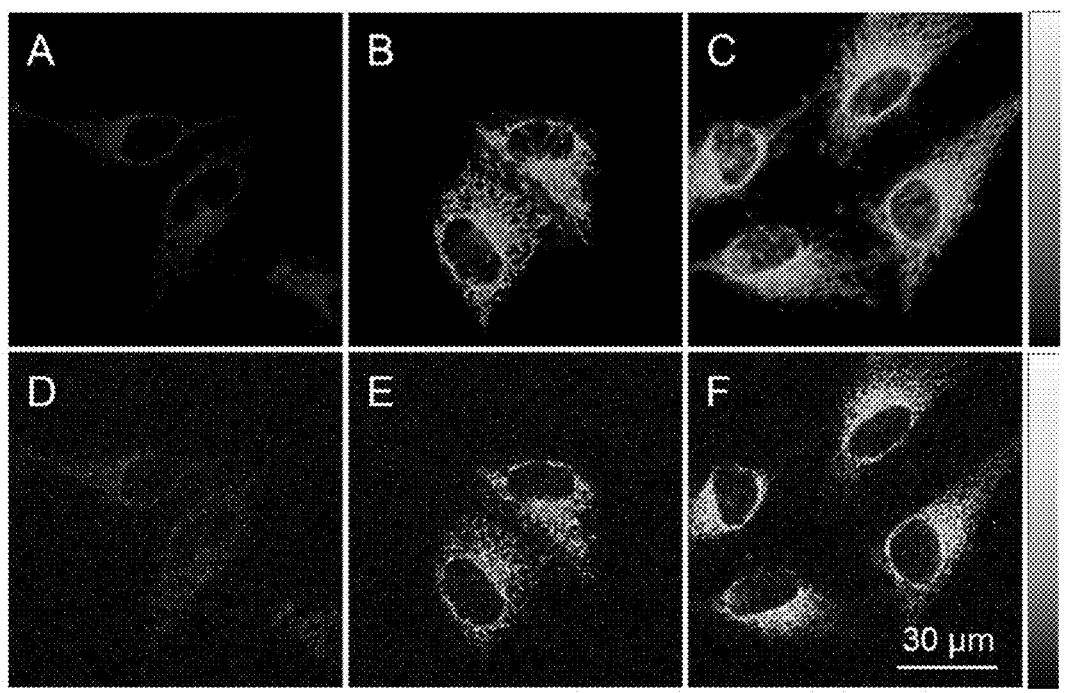
FIG. 12A is a fluorescent image of HeLa cells stained with 10 μM of AIE-SRS-Mito for 30 min.
FIG. 12B is a fluorescent image of HeLa cells stained with 20 μM of AIE-SRS-Mito for 30 min.
FIG. 12C is a fluorescent image of HeLa cells stained with 40 μM of AIE-SRS-Mito for 30 min.
FIG. 12D is an SRS image of HeLa cells stained with 10 μM of AIE-SRS-Mito for 30 min.
FIG. 12E is an SRS image of HeLa cells stained with 20 μM of AIE-SRS-Mito for 30 min.
FIG. 12F is an SRS image of HeLa cells stained with 40 μM of AIE-SRS-Mito for 30 min.

Since AIE-SRS-Mito demonstrated dual-mode imaging via TPEF and SRS, the correlation of fluorescence intensity and SRS signal intensity of HeLa cells stained with 20 µM AIE-SRS-Mito for 30 min was studied. At first, as shown in FIGS. 9A-9D, images of HeLa cells were collected by TPEF and SRS signals, respectively, and the merged image indicated a perfect co-localization of the intracellular distribution of the fluorescence and SRS signals, confirming the dual-modality of the probe. Statistical analysis shows that regions with high fluorescence intensities often have high SRS intensities, as verified by the positive correlation of TPEF intensity and SRS signal (interpreted as dye concentration) (FIGS. 10A-10B). Due to the inertness of SRS signal and the linear relationship ($I_{SRS}$=0.1567 c), the distribution of the dye concentration inside a single cell was further analyzed. As shown in FIG. 10D, the local concentration within a cell can be up to 1.5 mM, which is 75 folds higher than incubation concentration (20 μM).

To examine the influence of intracellular concentration of AIE-SRS-Mito on the cells, attempts were made to increase the amounts of dye in the cells by increasing the incubation time. As shown in FIGS. 11A-11F, with the extension of incubation time, both the TPEF and SRS intensity were increased with a reduced mitochondrial selectivity. Close examination of the cell images revealed that the linear reticulum-like morphology of mitochondria shrank into granules, indicating an unhealthy state of mitochondria. This can be attributed to the fact that the high concentration of cationic dyes in the mitochondria matrix will cause depolarization and increase the osmotic stress of the mitochondria, consequently leading to cell death as indicated by the results of the MTT assay (FIG. 4E). Similar results were found when increasing the dye concentration (FIGS. 12A-12F).

To further study acceptable intracellular concentrations of the dye molecules in a cell, the distribution of the dye concentration for cells was plotted. The percentages of high concentration region (>0.5 mM) were calculated to be 16.7%, 23.9% and 30.0% for the cells incubated with 20 μM of AIE-SRS-Mito for 30, 60 and 105 min, respectively. The ultimate high concentration within the cells was estimated to be 1.5, 2.0, 3.0 mM, respectively, covering >99.5% cell area. Taking the heathy state of the cells into account, the results suggested that HeLa cells can tolerate a high dye concentration of up to 3.0 mM in mitochondria matrix with moderate cell viability. Such a high concentration is enough to cause the quenching of Rhodamine 123 in cells.

The TPEF intensity of AIE-SRS-Mito exhibited a positive correlation with SRS signal (dye concentration) among all the observed cells. It is believed that TPEF intensity of AIE-SRS-Mito can be utilized for qualitatively comparing the intracellular concentration without fear of an ACQ problem. This should also be applicable to other AIE molecules. The present teachings set forth a method for determination of intracellular concentration of AIEgens with high spatial resolution and non-invasiveness.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A probe for dual-mode bioimaging, comprising a compound having a backbone structural formula of:

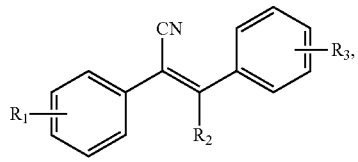

wherein $R_1$ is

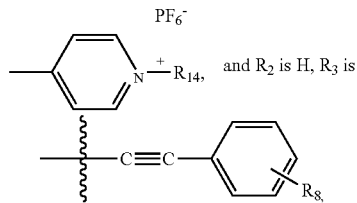

and $R_2$ is H, $R_3$ is $R_8$ is H, and $R_{14}$ is independently selected from the group consisting of H, heteroatom, alkyl, unsaturated alkyl, heteroalkyl, cycloalkyl, heterocycloalkyl, aryl, and heteroaryl.

2. The probe for dual-mode bioimaging according to claim 1, wherein the compound is:

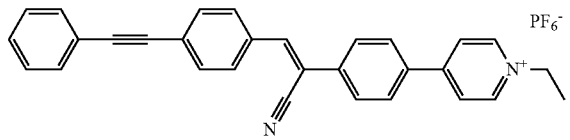 [SMILES: CC[n+]1ccc(-c2ccc(/C(C#N)=C/c3ccc(C#Cc4ccccc4)cc3)cc2)cc1 ; "PF6-"]

3. A method of cellular imaging, comprising:
contacting a target cell with a compound having a backbone structural formula of:

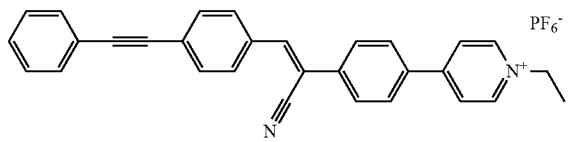 [SMILES: CC[n+]1ccc(-c2ccc(/C(C#N)=C/c3ccc(C#Cc4ccccc4)cc3)cc2)cc1 ; "PF6-"]

and identifying a target of interest in the target cell using an imaging method comprising at least one of fluorescence microscopy and Raman microscopy.

4. The method of cellular imaging according to claim 3, wherein the imaging method comprises both fluorescence microscopy and Raman microscopy.

5. The method of cellular imaging according to claim 3, wherein the Raman microscopy is selected from the group consisting of spontaneous Raman scattering microscopy, stimulated Raman scattering microscopy, and coherent anti-stokes Raman scattering microscopy.

6. The method of cellular imaging according to claim 3, wherein the fluorescence microscopy comprises two-photon excitation microscopy.

7. The method of cellular imaging according to claim 3, wherein the fluorescence microscopy comprises one-photon excitation microscopy.

8. The method of cellular imaging according to claim 3, wherein an intracellular concentration of the compound can be determined qualitatively from a fluorescence intensity.

9. The method of cellular imaging according to claim 3, wherein an intracellular concentration of the compound can be determined quantitatively from a stimulated Raman scattering signal intensity.

10. The method of cellular imaging according to claim 3, wherein the target of interest in the target cell comprises at least one of a biomolecule, a drug, a protein, and a cellular organelle of the target cell.

11. The method of cellular imaging according to claim 10, wherein the cellular organelle comprises a mitochondrion.

12. A probe for dual-mode bioimaging, comprising a compound having the following structural formula:

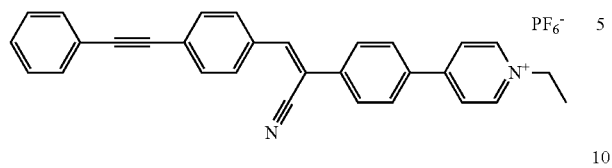

13. A method of cellular imaging, comprising:
contacting a target cell with the compound of claim 12; and
identifying a target of interest in the target cell using an imaging method comprising at least one of fluorescence microscopy and Raman microscopy.

14. The method of cellular imaging according to claim 13, wherein the imaging method comprises both fluorescence microscopy and Raman microscopy.

15. The method of cellular imaging according to claim 13, wherein the Raman microscopy is selected from the group consisting of spontaneous Raman scattering microscopy, stimulated Raman scattering microscopy, and coherent anti-stokes Raman scattering microscopy.

\* \* \* \* \*